United States Patent [19]

Nothacker

[11] Patent Number: 5,789,232
[45] Date of Patent: Aug. 4, 1998

[54] PROCESS FOR ISOLATING A VIRAL ANTIGEN PREPARATION

[75] Inventor: Klaus-Dieter Nothacker, Schmachthagen, Germany

[73] Assignee: Behring Diagnostics GmbH, Marburg, Germany

[21] Appl. No.: 750,742

[22] PCT Filed: Jun. 22, 1995

[86] PCT No.: PCT/EP95/02422

§ 371 Date: Dec. 20, 1996

§ 102(e) Date: Dec. 20, 1996

[87] PCT Pub. No.: WO96/00083

PCT Pub. Date: Jan. 4, 1996

[30] Foreign Application Priority Data

Jun. 24, 1994 [DE] Germany .................. 44 22 238.6

[51] Int. Cl.⁶ .................................................. C12N 7/00
[52] U.S. Cl. .................................. 435/239; 435/235.1
[58] Field of Search .............................. 435/239, 235.1

[56] References Cited

U.S. PATENT DOCUMENTS 3,514,374  5/1970  McAleer et al. .
4,100,267  7/1978  Shaw .

FOREIGN PATENT DOCUMENTS 0 190 972  8/1986  European Pat. Off. .

OTHER PUBLICATIONS

Natalie E. Cremer, Cynthia K. Cossen, Gordon Shell, Janice Diggs, Dana Gallo, and Nathalie J. Schmidt, "Enzyme Immunoassay Versus Plaque Neutralization and Other Methods for Determination of Immune Status to Measles and Varicella–Zoster Viruses and Versus Complement Fixation for Serodiagnosis of Infections with Those Viruses," Journal of Clinical Microbiology, Jun. 1985, pp. 869–874.

Matti Lehtinen, Vesa Koivisto, Tuula Lehtinen, Jorma Paavonen, Pauli Leinikki, "Immunoblotting and Enzyme–Linked Immunosorbent Assay Analysis of Serological Responses in Patients Infected with Herpes Simplex Virus Types 1 and 2," Intervirology 24: 18–25 (1985).

Von Andrea Lindner, H. Liebermann and H. Ambrosius, "Entwicklung eines Enzyme–linked Immunosorbent Assay zum Nachweis von Antikörpern gegen das Bovine Herpesvirus vom Typ 5 (BHV–5) in Schafseren," Deutsche Tierärztliche Wochenschrift, Mai 1993, 100, pp. 390–395.

K.–Q. Wang, C.M. Nielsen, B.F. Vestergaard, "Isolation and Adaptation Characteristics of Hepatitis A Virus in Primary African Green Monkey Kidney Cells: Production of Antigen Useful for ELISA Serology," Intervirology 24: 99–107 (1985).

*Primary Examiner*—Leon B. Lankford, Jr.
*Attorney, Agent, or Firm*—Finnegan, Henderson, Farabow, Garrett & Dunner, L.L.P.

[57] ABSTRACT

The present invention relates to a process for preparing antigens of viral origin from infected animal cells and to the use thereof in enzyme-linked immunosorbent assays (ELISAs). The process utilizes homogenization, centrifugation and an alkaline glycene buffer.

4 Claims, No Drawings

PROCESS FOR ISOLATING A VIRAL ANTIGEN PREPARATION

The present invention relates to a process for preparing antigens of viral origin from infected animal cells and to the use thereof in enzyme-linked immunosorbent assays (ELISAs).

In modern immunodiagnosis on patients' sera it is a proven and widely used technique to determine the antibody status against a wide variety of antigens, for example with the aid of an ELISA. This entails microtiter plates being coated with the antigen against which antibodies are to be detected, and subsequently being incubated with serum. If antigen-specific antibodies are present, they bind to the offered antigen and can then be detected by a detection system with, for example, peroxidase-conjugated anti-antibodies via an enzyme-mediated substrate conversion with development of a color which can be measured by photometry.

Preferably employed for producing antigens for coating the plates are animal cell cultures which form the required product or can be stimulated thereto. To establish the humoral immunity status against certain virus specificities using a suitable ELISA, for example cell cultures are infected with the appropriate viruses and harvested some time later, when the infection has affected the entire cell lawn. The infected cells are then starting material for preparing the viral antigen required for coating the assay plates.

N. E. Cremer et al., J. Clin. Microbiol. 21, pages 869–874 (1985) describe preparing antigens from cultures infected with varicella zoster virus (VZV)—a representative of the human herpesviruses—in such a way that cell homogenates are prepared from animal cells by disruption with ultrasound or multiple freeze/thaw treatment, which then contain nuclei and cytosolic constituents in suspension. The medium chosen for taking up the cells before the disruption treatment is isotonic phosphate-buffered saline (PBS) or alkaline glycine buffer. The resulting cell homogenates are subjected to a low-speed clarifying centrifugation in order to sediment cell nuclei and other larger constituents. The removed supernatants from the centrifugation—referred to as (cell) homogenate antigens hereinafter—can then be employed without further purification for coating microtiter plates for the ELISA. The preparation of antigens as described, for example, by M. Lehtinen et al., Intervirology 24, pages 18–25 (1985) from cells infected with herpes simplex virus (HSV) for the ELISA for detecting anti-HSV antibodies comprises comparable process steps. The procedure for hepatitis A virus (HAV) according to the principle described above is reported by K.-Q. Wang et al., Intervirology 24, 99–107 (1985).

Although cell homogenate (extract) antigens prepared according to the prior art can be used, they contain a very large proportion of cellular proteins which are immunologically irrelevant or even interfere and, during the coating of microtiter plates, compete with the viral proteins and structures required for covering the solid phase, so that the occupation density of the polystyrene surface with virus-specific components is prematurely limited. This competition is also the reason why no further increase in sensitivity (signal) is possible in the ELISA through a more highly concentrated homogenate antigen for coating.

The present invention was therefore based on the object of considerably reducing, with use of a suitable buffer in processing the antigen, the content of cellular proteins present in the cell homogenate in order thus to increase the occupation density for virus-specific components on the solid phase. This is a crucial pre-condition for being able to improve assay properties such as sensitivity and positive predictive value with an unchanged specificity and as far as possible at the same time employing a more economic amount of antigens for coating assay plates.

It has been possible to achieve this object by an isolation process in which the concentration of cellular organelles (especially cell nuclei) and proteins is decreased and that of viral constituents is increased by a differential centrifugation of virus-containing cell homogenate antigen which is obtained by ultrasonic treatment of VZV infected cells taken up in glycine buffer. The pellets obtained after an ultracentrifugation and containing virions, capsids and precursors of the virus assembly are resuspended in buffer with the assistance of ultrasound. It is possible with the antigen obtained in this way, referred to as "UC pellet" antigen hereinafter, by comparison with the homogenate antigen hitherto used

- drastically to improve ELISA properties such as sensitivity and P/N ratio, with a considerably increased signal reserve,
- to reduce the proportion of faulty batches in the processing of antigen because even weaker crude antigens serving as starting material can be processed with great prospects of success to high-quality antigens,
- to achieve an effective saving in the use of crude antigen, through greatly increased coating dilutions, whereby the effort for cell culturing is considerably reduced,
- to keep the effort for processing on the production scale practically and economically acceptable.

The invention therefore relates to a process for the preparation of antigens of viral origin from infected animal cells, the process including the following steps:

a) ultrasonic homogenization of infected cells, b) at least one low-speed centrifugation to remove impurities and c) at least one ultracentrifugation to isolate the antigen.

A preferred process in this connection is one in which a glycine buffer, preferably a glycine buffer of pH 7–10, is used in at least one of steps a)-c).

A preferred process is also one in which the ultracentrifugation takes place at 54,000 to 64,000×g.

A further preferred process in one in which another centrifugation at 5,000–10,000×g is interpolated between step b) and c).

The virus employed is preferably a herpes-, hepatitis- or mumpsvirus.

The invention furthermore relates to the use of the antigen preparations obtained by one of the processes described above for coating solid phases such as, for example, microtiter plates or particles such as latices.

The starting material for preparing VZV antigens by the process according to the invention are VZV-infected, diploid human fibroblasts which are cultivated, infected, incubated and harvested in accordance with published instructions.

An advantageous embodiment of the process according to the invention is one in which 1 part of cell sediment (for example measured in a graduated conical tube) is resuspended in 1.5–5, preferably 1.5–2, parts of distilled water or glycine buffer (0.1 M glycine, 0.1 M NaCl, pH 7–10, preferably 9–10, very preferably 9.5) and treated with ultrasound in an ice bath (Labsonic U-2000 ultrasonic homogenizer from B. Braun Diessel Biotech GmbH, intermediate probe, power set at 20–60, preferably 30–50, W, where appropriate needle probe preferably with about 50 W). The duration and frequency of the ultrasonic pulses are known to the skilled worker per se or, where appropriate, can easily be determined by simple tests. Preferred for volumes of, for example, about 10–50 ml are a sonication time of ½–2 min and a sonication frequency of about 3–5 intervals. In order to ensure that the energy input is always sufficient, the material to be sonicated should not exceed about 50 ml, depending on the ultrasound emitter used. The ultrasonic treatment can take place, for example, in 50 ml conical tubes (for example Greiner, PP, 50 ml) to guarantee that the steric conditions are as comparable as possible. After addition of a further 28–36 parts of glycine buffer (based on the volume of cell sediment), the diluted cell homogenate which is then present is inactivated by adjusting to 0.05–0.1%, advantageously 0.06%, β-propiolactone and incubating at 2°–8° C. for 10 min–16 h and then at 37° C. for 120±10 min. The cell homogenate, which is no longer infectious due to this treatment, is pelleted at low speed, 300–500×g, and 2°–8° C. for 10±2 min in order to remove unlyzed cells, cell fragments and nuclei. The removed supernatant from the centrifugation is subjected to a high-speed centrifugation at 40,000–100,000×g, preferably 54,000–64,000×g, and at 2°–8° C. for 120±30 min (for example in a Centricon T2050 ultracentrifuge from Kontron in a 50.2 Ti or 45 Ti rotor).

The pellet obtained by ultracentrifugation is resuspended in, preferably, glycine buffer (see above) in a volume which is 0.05–0.5 times the amount of homogenate after inactivation, with assistance from ultrasound in 0.5–1.5 minute pulses (LABSONIC U-2000 ultrasonic homogenizer from B. Braun Diessel Biotech GmbH, intermediate probe or needle probe, power set at 20–90 W) until a uniform suspension is present.

We find that the concentration of viral constituents in the "UC pellet" antigen obtained in this way is increased and that of cellular proteins is decreased.

Crucially important for the process is, besides the ultracentrifugation, the buffer employed for preparing the cell homogenate during the UC run and for resuspension of the virus pellet. The use of this buffer in preparing VZV or mumps "UC pellet" antigen makes it possible to increase the quality in the ELISA further.

The advantages of the process according to the invention are also particularly evident from comparison with the prior art.

The increase in the concentration of viral constituents by differential centrifugation after homogenization of VZV-infected cells results in an antigen which, when it is used for the ELISA, not only makes very evident improvements in quality possible by comparison with the cell homogenate antigen produced in accordance with the prior art, but also has considerable advantages in terms of quantity and economy.

Tab. 1 shows the coating according to the invention with the VZV antigen preparation by comparison with the prior art. "UC pellet" antigen and homogenate antigen were prepared starting from the same cellular starting material. They were diluted 1:20, 40, 80, 160, 320, 640, 1,280, 2,560 and 5,120 with PBS and then employed for direct coating of microtiter assay plates (96 wells) with 100 µl/well. The "homogenate" corresponds to the prior art.

In the case of "UC pellet" material, besides an antigen which was concentrated 10-fold by comparison with the initial homogenate volume, use was also made of an antigen concentrated only 2-fold.

After antigen adsorption, an anti-VZV IgG-positive and an anti-VZV IgG-negative serum was assayed at the various dilution levels. The procedure for this assay corresponded to the protocol set forth in the pack insert for the commercial ELISA product of Behringwerke AG, Enzygnost® anti-VZV/IgG (assay plate), product No. OWLU, with a serum dilution of 1:231.

The samples were incubated with the solid-phase antigen, the unbound antibodies were washed out, an enzyme was bound via a conjugate solution to the antibody/antigen complexes formed, the excess conjugate solution was washed out, a chromogenic substrate solution was used to form the color via the enzyme, and subsequently the reaction was stopped with a stop solution. The samples prepared in this way, with a color depending on the content of the virus-specific antibodies, were then evaluated by determining their extinction (E) by photometry at 450 nm.

Tab. 1 a) shows the extinctions in mE for the two sera obtained with the individual antigen presentations.

Tab. 1 b) shows the corresponding P/N ratios (ratios between the extinctions of the positive serum and negative serum at each dilution level). If the ratios for the "UC pellet" antigen in the ELISA-relevant dilution range of 1:20–1:320 (2-fold concentrate) or 1:40–1:1280 (10-fold concentrate) are 9.0–13.7 (mean x=11.8+1.4), the homogenate antigen remains far behind this, with its P/N ratios of 3.2–4.9 (x=4.2+0.8) in the dilution range of 1:20–1:160. Immunodiagnosis in the ELISA is distinctly improved by the "UC pellet" antigen since the discrimination of positive and negative sera is optimized and the proportion of false-negative sera is reduced (increase in sensitivity).

The "UC pellet" antigen has a noticeably large signal reserve. While a maximum OD of 651 mE is reached with the positive serum in the case of the homogenate antigen, extinctions of up to 1,300–1,600 mE are possible with the "UC pellet" antigen. Moreover the reaction of the negative serum as far as the dilution range of 1:80 is in fact below the OD of 134 mE in the case of the homogenate antigen diluted 1:20. The 130 mE range is then reached only with 1:20 (2-fold "UC pellet" concentrate) or 1:40 (10-fold "UC pellet" concentrate). Thus, in this situation, it is possible by using "UC pellet" antigen to double the level of extinction with positive sera from, for example, about 650 mE to about 1,300 mE, without losing specificity in the negative reaction.

Comparable results are also found in the IgM assay (Tab. 1 c) and d)). The coating dilutions were chosen as for the IgG assay. The assay was carried out in accordance with the pack insert for Enzygnost® anti-VZV/IgM (assay plate), product No. OWLX, with a serum dilution of 1:42. The "UC pellet" antigen permits OD values of up to 2,000 mE with the anti-VZV IgM-positive serum. In the case of homogenate antigen, a maximum of 624 mE, which was reached with the 1:20 antigen dilution, is not exceeded and, at the same time, the reaction of the negative serum in the ELISA-relevant dilution range of 1:20–1:80 is about 150 mE. The "UC pellet" antigen is distinguished therefrom by OD values of about 1400 mE with the 2-fold concentrate and about 1700 mE (interpolated) with the 10-fold concentrate in the case of positive serum, while the extinction for the negative serum is identical (Tab. 1 c)). This means that, while the specificity is unchanged, the level of extinction for the positive serum is more than doubled by comparison with the homogenate antigen.

Corresponding results are found for the P/N ratios (Tab. 1 d) ) . The "UC pellet" antigen shows ratios of 7.1–9.6 (x=8.8+1.5) for dilutions of 1:40–1:640 with the 2-fold concentrate, and ratios of 6.0–10.9 (x=8.8±1.8) in the dilution range of 1:40–1:5,120 with the 10-fold concentrate. The homogenate contrasts greatly with ratios of 1.9–4.2 (x=3.2±1.2) for the 1:20–1:80 antigen dilutions of interest. As in the IgG assay, this means that the requirement of generally improving the discrimination between positive and negative sera and reducing the proportion of false-negative sera without losing specificity is met (increase in sensitivity).

It is also possible by the process according to the invention to prepare suitable antigens from weaker starting materials (infected cells)—which it was necessary to discard in the prior art.

Aiming at the minimum OD specification which is customary for homogenate antigens with the IgG-positive serum of about 650 mE for calculation by interpolation of the maximum possible dilution of an antigen for coating results in factors of 1:20 for the homogenate, 1:249 for the 2-fold and 1:882 for the 10-fold "UC pellet" concentrate (Tab. 2). Taking account of the concentration factors in the preparation of antigens by differential centrifugation, use is 4–6 times more economic in the case of the "UC pellet" antigen by comparison with the homogenate when the properties and requirements of the assay are left unchanged for the time being. While the effort for cell cultivation to prepare the starting material (crude antigen) remains the same, it is accordingly possible by using "UC pellet" antigen to coat 4–6 times more assay plates with antigen than previously. A corresponding statement applies to the IgM assay.

Table 2 also shows the P/N ratios derived from the calculated coating dilutions. They make it clear that the extinctions with the negative sera can be reduced by a factor of 2–4 with "UC pellet" antigen when the positive reactions are adjusted to be identical to the homogenate antigen. This means that it is also possible to conceive an improvement in the assay by correcting the cutoff value downwards so that previously false-negative sera show a correct positive reaction.

The use of an alkaline glycine buffer in the "UC pellet" antigen preparation from VZV-infected cells has very advantageous effects by comparison with the use of a pH-neutral physiological phosphate buffer (PBS). Tab. 3 shows this by the extinctions measured with 3 IgG-positive and one -negative serum after comparative processing with the two buffers in accordance with the protocol described under 1 b).

The following examples are intended to illustrate the invention but not restrict it in any way.

EXAMPLES

1. Preparation of the "UC pellet" antigen from varicella zoster (VZV)-infected cells a) 7.2 ml of a cell sediment were resuspended in 10.8 ml of distilled water and treated with ultrasound in an ice bath for 4×1 min (LABSONIC U-2000 ultrasonic homogenizer from B. Braun Diessel Biotech GmbH at 50 W, needle probe). After the homogenization, 202 ml of glycine buffer (0.1 M glycine, 0.1 M NaCl, pH 9.5±0.5) were added. Subsequently, β-propiolactone was pipetted in to a final concentration of 0.06%, and the mixture was incubated, stirring gently, first at 4° C. for 10 min and then at 37° C. for 120 min. It was subsequently centrifuged at 500×g for 10 min (at 4° C.). The supernatant from the centrifugation was removed and subjected to a centrifugation at 54.000×g at a temperature of 4° C. for 120 min. The pellet resulting from this was taken up in 24 ml of glycine buffer and resuspended with ultrasonic assistance.

b) 3 ml of a cell sediment were suspended in 12 ml of glycine buffer and treated with ultrasound in an ice bath for 4×1 min (LABSONIC U-2000 ultrasonic homogenizer from B. Braun Diessel Biotech GmbH at 20 W, intermediate probe). After the homogenization, 84 ml of glycine buffer (0.1 M glycine, 0.1 M NaCl, pH 9.5±0.5) were added. Subsequently, β-propiolactone was pipetted in to a final concentration of 0.06%, and the mixture was incubated, stirring gently, first at 4° C. for 10 min and then at 37° C. for 120 min. It was subsequently centrifuged at 300×g for 10 min (at 4° C.). The supernatant from the centrifugation was removed and subjected to a centrifugation at 64.000×g at a temperature of 4° C. for 120 min.

The pellet resulting from this was taken up in 11 ml of glycine buffer and resuspended with ultrasonic assistance.

c) Processing took place exactly as in 1 b) with the modification that glycine buffer was replaced by PBS in each case.

2. Preparation of "UC pellet" antigen from herpes simplex virus (HSV)-infected cells 5.7 ml of a sediment of vero cells infected with HSV were resuspended in 9 ml of distilled water and treated with ultrasound in an ice bath for 4×1 min (LABSONIC U-2000 ultrasonic homogenizer from B. Braun Diessel Biotech GmbH at 20 W, intermediate probe). After the homogenization, 168 ml of glycine buffer were added. Subsequently, β-propiolactone was pipetted in to a final concentration of 0.06%, and the mixture was incubated, stirring gently, first at 4° C. for 10 min and then at 37° C. for 120 min. It was subsequently centrifuged at 500×g for 10 min (at 4° C.). The supernatant from the centrifugation was removed and subjected to a centrifugation at 54.000×g at a temperature of 4° C. for 120 min. The pellet resulting from this was taken up in 10 ml of glycine buffer and resuspended with ultra sonic assistance.

Tab. 4 summarizes the extinctions measured with 6 positive and one negative serum. On formation of the P/N ratios by summing the extinctions of 4 positive sera in each case and dividing by the relevant OD of the negative serum, the homogenate antigen then shows an average P/N ratio of 20.2±1.4 (dilution range 1:100–1:1800), whereas the average ratio with the "UC pellet" antigen is almost 1.5 times higher at 29.5±3.5. This means a gain in sensitivity with the same specificity, or a gain in specificity when the sensitivity is adjusted identically.

The rating for the IgM assay results is very similar. In this case, the homogenate antigen has an average P/N ratio of 16.2±2.6 by comparison with a ratio which is 2.1 times higher, 34.6±2.8, with the "UC pellet" antigen.

3. Preparation of "UC pellet" antigen from hepatitis A virus (HAV)-infected cells 7.5 ml of a cell sediment from human fibroblasts infected with HAV were resuspended in 15 ml of glycine buffer and treated with ultrasound in an ice bath for 4×1 min (LABSONIC U-2000 ultrasonic homogenizer from B. Braun Diessel Biotech GmbH at 35 W, intermediate probe). After the homogenization, 210 ml of glycine buffer were added. Subsequently, β-propiolactone was pipetted in to a final concentration of 0.1%, and the mixture was incubated, stirring gently, first at 40° C. for 16 h and then at 37° C. for 120 min. It was subsequently centrifuged at 300×g for 10 min (at 4° C.). The supernatant from the centrifugation was removed and subjected to a centrifugation at 54,000×g at a temperature of 40° C. for 120 min. The pellet resulting from this was taken up in 12.5 ml of glycine buffer and resuspended with ultrasonic assistance.

The antigens were coated onto the surface of wells of microtiter plates, using a polyclonal trapping antibody for HAV in dilution levels of 1:10, 1:50 and 1:100 in PBS, and then assayed in the ELISA. Tab. 5 summarizes the extinctions measured with an undiluted positive serum. Only with the "UC pellet" antigen is a desirable extinction of ≧1000 mE still far exceeded with an antigen dilution of 1:100, whereas the homogenate antigen does not quite reach this level even with the 1:10 antigen dilution. This means that the "UC pellet" material, taking the concentration factor of 20 into account in the calculation, can be employed far more than 5 times more economically than the homogenate antigen. In addition, it provides a large signal reserve which makes it possible to develop a considerably more sensitive assay than with homogenate antigen. Whereas faulty batches are unavoidable in the case of weaker starting material with homogenate antigen, there will be hardly any rejects on preparation of antigens by differential centrifugation.

4. Use of glycine buffer in the preparation of mumps "UC pellet" antigen a) 4 ml of a cell sediment were resuspended in 16 ml of glycine buffer and treated with ultrasound in an ice bath for 4×1 min (LABSONIC U-2000 ultrasonic homogenizer from B. Braun Diessel Biotech GmbH at 20 W, intermediate probe). After the homogenization, 144 ml of glycine buffer were added. Subsequently, β-propiolactone was pipetted in to a final concentration of 0.06%, and the mixture was incubated, stirring gently, first at 4° C. for 10 min and then at 37° C. for 120 min. It was subsequently centrifuged at 300×g for 10 min (at 4° C.). The supernatant from the centrifugation was removed and subjected to a centrifugation at 64,000×g at a temperature of 4° C. for 120 min. The pellet resulting from this was taken up in 13 ml of glycine buffer and resuspended with ultrasonic assistance.

b) Processing took place exactly as in 4 a) with the modification that the glycine buffer was replaced by PBS in each case.

Use of alkaline glycine buffer shows a distinct improvement in the antigen by comparison with PBS. Thus, the antigen coating dilution which can be calculated after use of glycine buffer is about 1:2000, whereas it is only about 1:600 after use of PBS.

TABLE 1 a)

Extinction (mE) in the ELISA with an anti-VZV-positive and -negative IgG serum after coating of assay plates with VZV homogenate and UC pellet antigen in the stated dilutions

| VZV antigen | IgG serum | | Antigen coating dilution 1: | | | | | | | |
|---|---|---|---|---|---|---|---|---|---|---|
| | No. | pos./neg. | 20 | 40 | 80 | 160 | 320 | 640 | 1280 | 2560 |
| Homogenate | 413124A | pos. | 651 | 497 | 345 | 176 | 89 | 40 | 21 | 11 |
| | 123948 | neg. | 134 | 104 | 91 | 55 | 39 | 26 | 21 | 11 |
| UC pellet (2-fold conc.) | 413124A | pos. | 1607 | 1569 | 1294 | 900 | 452 | 167 | 61 | 27 |
| | 123948 | neg. | 133 | 141 | 96 | 70 | 43 | 24 | 15 | 11 |
| UC pellet (10-fold conc.) | 413124A | pos. | 1335 | 1291 | 1192 | 1252 | 1138 | 778 | 442 | 184 |
| | 123948 | neg. | 231 | 144 | 116 | 108 | 83 | 63 | 36 | 20 |

TABLE 1 b)

P/N ratios calculated from the extinctions in Tab. 1 a)

| VZV antigen | Antigen coating dilution 1: | | | | | | | |
|---|---|---|---|---|---|---|---|---|
| | 20 | 40 | 80 | 160 | 320 | 640 | 1280 | 2560 |
| Homogenate | 4.9 | 4.8 | 3.8 | 3.2 | 2.9 | 1.5 | 1.0 | 1.0 |
| UC pellet (2-fold conc.) | 12.1 | 11.1 | 13.5 | 12.9 | 10.5 | 7.0 | 4.1 | 2.5 |
| UC pellet (10-fold conc.) | 5.8 | 9.0 | 10.3 | 11.6 | 13.7 | 12.3 | 12.3 | 9.2 |

TABLE 1 c)

Extinction (mE) in the ELISA with an anti-VZV-positive and -negative IgM serum after coating of assay plates with VZV homogenate and UC pellet antigen in the stated dilutions

| VZV antigen | IgM serum | | Antigen coating dilution 1: | | | | | | | | |
|---|---|---|---|---|---|---|---|---|---|---|---|
| | No. | pos./neg. | 20 | 40 | 80 | 160 | 320 | 640 | 1280 | 2560 | 5120 |
| Homogenate | 413124 | pos. | 624 | 553 | 304 | 246 | 209 | 122 | 54 | 33 | 50 |
| | 123.948 | neg. | 148 | 158 | 160 | 113 | 115 | 101 | 55 | 29 | 70 |

TABLE 1 c)-continued

Extinction (mE) in the ELISA with an anti-VZV-positive and -negative IgM serum after coating of assay plates with VZV homogenate and UC pellet antigen in the stated dilutions

| VZV antigen | IgM serum No. | pos./neg. | Antigen coating dilution 1: | | | | | | | | |
|---|---|---|---|---|---|---|---|---|---|---|---|
| | | | 20 | 40 | 80 | 160 | 320 | 640 | 1280 | 2560 | 5120 |
| UC pellet (2-fold conc.) | 413124 | pos. | 1413 | 1972 | 1419 | 1605 | 824 | 414 | 157 | 67 | 37 |
| | 123.948 | neg. | 246 | 279 | 186 | 178 | 76 | 43 | 35 | 25 | 20 |
| UC pellet (10-fold conc.) | 413124 | pos. | 1442 | 1607 | 1813 | 1974 | 1855 | 1736 | 1187 | 558 | 253 |
| | 123.948 | neg. | 479 | 227 | 187 | 204 | 203 | 159 | 109 | 76 | 42 |

TABLE 1 d)

P/N ratios calculated from the extinctions in Tab. 1 c)

| VZV antigen | Antigen coating dilution 1: | | | | | | | | |
|---|---|---|---|---|---|---|---|---|---|
| | 20 | 40 | 80 | 160 | 320 | 640 | 1280 | 2560 | 5120 |
| Homogenate | 4.2 | 3.5 | 1.9 | 2.2 | 1.8 | 1.2 | 1.0 | 1.1 | 0.7 |
| UC pellet (10-fold conc.) | 3.0 | 7.1 | 9.7 | 9.7 | 9.1 | 10.9 | 10.9 | 7.3 | 6.0 |
| UC pellet (2-fold conc.) | 5.7 | 7.1 | 7.6 | 9.0 | 10.8 | 9.6 | 4.5 | 2.7 | 1.9 |

TABLE 2

Coating dilutions for VZV UC pellet and homogenate antigens aiming at preset minimum OD specifications with the positive sera mentioned in Tabs. 1 and 3

| Assay | VZV antigen | Antigen coating dilution | | Ag. dil. UC pellet / Ag. dil. homogenate | P/N ratio with Ag coating dilution |
|---|---|---|---|---|---|
| | | for 650 mE (IgG) or 390 mE (IgM) | taking account of the concentration factor in the calculation | | |
| IgG | Homogenate | 20 | 20 | — | 4.9 |
| | UC pellet (2-fold conc.) | 249 | 125 | 6.25 | 12.3 |
| | UC pellet (10-fold conc.) | 882 | 88 | 4.4 | 11.8 |
| IgM | Homogenate | 66 | 66 | — | 2.5 |
| | UC pellet (2-fold conc.) | 700 | 350 | 5.3 | 10.0 |
| | UC pellet (10-fold conc.) | 3970 | 397 | 6.0 | 6.6 |

TABLE 3

Extinctions (mE) in the ELISA with 3 anti-VZV-positive and one -negative IgG serum after coating of assay plates with UC pellet antigen prepared in glycine buffer or PBS

| IgG serum | | Antigen coating dilution 1: | | | | | | | |
|---|---|---|---|---|---|---|---|---|---|
| | | Glycine buffer in Ag preparation | | | | PBS in Ag preparation | | | |
| No. | pos./neg. | 40 | 80 | 160 | 320 | 40 | 80 | 160 | 320 |
| 410828 | pos. | 1113 | 1025 | 811 | 652 | 977 | 942 | 770 | 507 |
| S-367 | pos. | 351 | 348 | 268 | 225 | 256 | 251 | 219 | 137 |
| S-361 | pos. | 290 | 305 | 252 | 174 | 233 | 227 | 206 | 146 |
| 123948 | neg. | 27 | 27 | 20 | 17 | 26 | 20 | 16 | 15 |

TABLE 4

Extinction (mE) in the ELISA with 6 anti-HSV-positive and one -negative IgG serum after coating of assay plates with HSV homogenate antigen and UC pellet antigen in the stated dilutions

| IgG serum | | Antigen coating dilution 1: | | | | | | | | | | | |
|---|---|---|---|---|---|---|---|---|---|---|---|---|
| | | UC pellet antigen | | | | | | | Homogenate antigen | | | | |
| No. | pos./neg. | 100 | 300 | 600 | 1800 | 3600 | 7200 | 14,400 | 100 | 300 | 600 | 1800 | 3600 |
| S-367 | pos. | >2100 | >2100 | >2100 | 1896 | 1703 | 1498 | 1043 | 1508 | 1245 | 1164 | 735 | 37 |
| S-356 | pos. | >2100 | 2006 | 1867 | 1556 | 1315 | 1002 | 621 | 951 | 756 | 601 | 362 | 0 |
| S-357 | pos. | 1839 | 1678 | 1625 | 1225 | 1134 | 708 | 483 | 768 | 546 | 505 | 246 | 0 |
| S-370 | pos. | 633 | 516 | 462 | 286 | 218 | 143 | 75 | 132 | 89 | 73 | 42 | 0 |
| 264008 | pos. | 530 | 439 | 467 | 332 | 340 | 189 | 126 | 231 | 165 | 124 | 91 | 30 |
| 406525 | pos. | 1314 | 1172 | 1228 | 866 | 750 | 504 | 331 | 500 | 472 | 316 | 188 | 85 |
| S-331 | neg. | 162 | 127 | 129 | 104 | 82 | 55 | 36 | 80 | 68 | 46 | 29 | 14 |

TABLE 5

Extinctions (mE) in the ELISA with an anti-HAV-positive IgG serum (42651NA) after coating of an assay plate with HAV homogenate antigen and UC pellet antigen in the stated dilutions

| HAV antigen | Antigen coating dilution 1: | | |
|---|---|---|---|
| | 10 | 50 | 100 |
| Homogenate | 946 | 443 | 353 |
| UC pellet (20-fold conc.) | 3651 | 3460 | 2536 |

I claim:

1. A process for the preparation of antigens of viral origin from infected animal cells, the process including the following steps:

a) ultrasonic homogenization of infected cells, b) at least one low-speed centrifugation at 300–500×g to remove impurities and c) at least one ultracentrifugation to isolate the antigen, where a glycine buffer, pH 9–10, is used in at least one of steps a)-c).

2. A process as claimed in claim 1, wherein the ultracentrifugation takes place at 54,000 to 64,000×g.

3. A process as claimed in claim 1, wherein another centrifugation at 5,000–10,000×g is interpolated between step b) and c).

4. A process as claimed in claim 1, wherein the virus is a herpes-, hepatitis- or mumpsvirus.

* * * * *